United States Patent [19]

Sommer et al.

[11] Patent Number: 5,264,426

[45] Date of Patent: Nov. 23, 1993

[54] PHOSPHORYLATED DIAZACYCLOALKANES

[75] Inventors: Herbert Sommer, Solingen; Jürgen Hartwig, Leverkusen, both of Fed. Rep. of Germany

[73] Assignee: Bayer Aktiengesellschaft, Leverkusen, Fed. Rep. of Germany

[21] Appl. No.: 947,232

[22] Filed: Sep. 18, 1992

[30] Foreign Application Priority Data

Sep. 30, 1991 [DE] Fed. Rep. of Germany ....... 4132492

[51] Int. Cl.$^5$ ..................... A01N 43/54; A01N 43/50; C07F 9/6512; C07F 9/6506
[52] U.S. Cl. ........................................ 514/94; 514/79; 514/86; 540/542; 544/243; 548/411
[58] Field of Search ........................ 548/411; 544/243; 540/542; 514/86, 94, 79

[56] References Cited

U.S. PATENT DOCUMENTS

| | | | |
|---|---|---|---|
| 3,812,144 | 5/1974 | Dietrich et al. | 260/309.7 |
| 4,590,182 | 5/1986 | Haga et al. | 514/92 |
| 4,880,933 | 11/1989 | Shiokawa | 548/411 |
| 4,900,838 | 2/1990 | Murdock | 548/411 |

FOREIGN PATENT DOCUMENTS

| | | |
|---|---|---|
| 0192060 | 1/1986 | European Pat. Off. |
| 464830 | 1/1992 | European Pat. Off. ............ 548/411 |
| 2376155 | 12/1977 | France . |

OTHER PUBLICATIONS

Chemical Abstracts, vol. 91, (1979,) 91: 157266t. (=DE-A 2,804,796).
Chemical Abstracts, vol. 89, (1978,) p. 607, 89: 23770c (=DE-A 2,642,982).
Chemical Abstracts, vol. 88, (1978,) p. 511, 88: 1046663 (=DE-A 2,615,342).
Chemical Abstracts, vol. 84, (1976,) p. 432, 84: 164413x (=DE-A 2,527,308).
Chemical Abstracts, vol. 78, (1973,) p. 417, 159604g (=DE-OS 2,144,013).
Chemical Abstracts, vol. 78, (1973,) p. 387, 136299x (=DE-OS 2,140,405).
Richard A. Houghten, "Bicyclic Guanidino Ketones" in J. Org. Chem., (1979,) pp. 4536-4543.
Franz Esser, "Cyclic Guanidines; I. Intramolecular Mercury(II)-Induced Amination of Alkenes as a Convenient Route to Bicyclic Guanidines," in *Synthesis*, (1987,) pp. 460-466.
P. B. M. W. M. Timmermans, "Dissociation Constants of Clonidines and Structurally Related Imidazolidines," in *Arzneim.-Forsch/Drug Res.*, (1978,) pp. 1676-1681.

Primary Examiner—Mark L. Berch
Attorney, Agent, or Firm—Sprung Horn Kramer & Woods

[57] ABSTRACT

The present invention relates to new phosphorylated diazacycloalkanes, to processes for their preparation, and to their use as pesticides, in particular as insecticides and nematicides. The new compounds have the general formula (I)

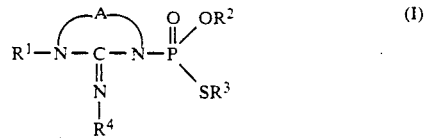

in which
R$^1$ represents hydrogen, or represents alkyl, alkenyl or aryl, each of which is optionally substituted by halogen or alkoxy,
A represents an alkanediyl radical which is optionally substituted by alkyl,
R$^2$ represents alkyl,
R$^3$ represents alkyl and
R$^4$ represents hydrogen, or represents alkyl, alkenyl or aryl, each of which is optionally substituted by halogen or alkoxy.

10 Claims, No Drawings

PHOSPHORYLATED DIAZACYCLOALKANES

The present invention relates to new phosphorylated diazacycloalkanes, to processes for their preparation, and to their use as pesticides, in particular as insecticides and nematicides.

It has been disclosed that certain phosphorylated aza compounds such as, for example, 0-ethyl S-(1-methylpropyl) (2-oxo-3-thiazolidinyl)-phosphorothioate/fosthiazate, can be used as insecticides, miticides and nematicides (compare U.S. Pat. No. 4,590,182). However, the action of these known compounds is not entirely satisfactory, in particular when low concentrations of active compound and amounts are applied.

The present invention relates to new phosphorylated diazacycloalkanes of the general formula (I)

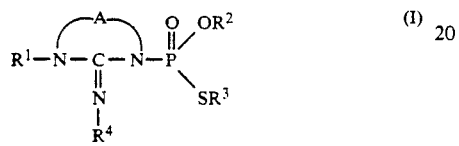

in which
- $R^1$ represents hydrogen, or represents alkyl, alkenyl or aryl, each of which is optionally substituted by halogen or alkoxy,
- A represents an alkanediyl radical which is optionally substituted by alkyl,
- $R^2$ represents alkyl,
- $R^3$ represents alkyl and
- $R^4$ represents hydrogen, or represents alkyl, alkenyl or aryl, each of which is optionally substituted by halogen or alkoxy.

Surprisingly, the compounds of the formula (I) according to the invention show a considerably more powerful insecticidal, in particular soil-insecticidal action, than the compound 0-ethyl S-(1-methylpropyl) (2-oxo-3-thiazolidinyl)-phosphorothioate, which is known, and, as opposed to active compounds of the prior art which have a similar structure, have a powerful activity against soil-dwelling insects as well as against soil-dwelling nematodes.

Formula (I) provides a general definition of the phosphorylated diazacycloalkanes according to the invention. In formula (I),

- $R^1$ preferably represents hydrogen; $C_1-C_8$-alkyl (which is optionally substituted by fluorine and/or chlorine or by $C_1-C_4$-alkoxy); $C_2-C_6$-alkenyl (which is optionally substituted by fluorine and/or chlorine or by $C_1-C_4$-alkoxy), or phenyl which is optionally monosubstituted to polysubstituted by identical or different substituents from the series comprising halogen and $C_1-C_4$-alkoxy,
- A preferably represents $C_2-C_4$-alkanediyl which is optionally monosubstituted or polysubstituted by identical or different substituents from the series comprising methyl and ethyl,
- $R^2$ preferably represents $C_1-C_8$-alkyl,
- $R^3$ preferably represents $C_1-C_{12}$-alkyl and
- $R^4$ preferably represents hydrogen; $C_1-C_8$-alkyl (which is optionally substituted by fluorine and/or chlorine or by $C_1-C_4$-alkoxy); $C_2-C_6$-alkenyl (which is optionally substituted by fluorine and/or chlorine or by $C_1-C_4$-alkoxy), or phenyl which is optionally monosubstituted to polysubstituted by identical or different substituents from the series comprising halogen and $C_1-C_4$-alkoxy.

In formula (I),
- $R^1$ particularly preferably represents hydrogen; $C_1-C_6$-alkyl (which is optionally substituted by fluorine and/or chlorine or by methoxy or ethoxy); vinyl, propenyl or butenyl (each of which is optionally substituted by fluorine and/or chlorine or by methoxy or ethoxy), or phenyl which is optionally monosubstituted to trisubstituted by identical or different substituents from the series comprising fluorine, chlorine, bromine, methoxy and ethoxy,
- A particularly preferably represents dimethylene or trimethylene, each of which is optionally monosubstituted or polysubstituted by identical or different substituents from the series comprising methyl and ethyl,
- $R^2$ particularly preferably represents $C_1-C_6$-alkyl,
- $R^3$ particularly preferably represents $C_1-C_{10}$-alkyl and
- $R^4$ particularly preferably represents hydrogen; $C_1-C_6$-alkyl (which is optionally substituted by fluorine and/or chlorine or by methoxy or ethoxy); vinyl, propenyl or butenyl (each of which is optionally substituted by fluorine and/or chlorine or by methoxy or ethoxy), or phenyl which is optionally monosubstituted to trisubstituted by identical or different substituents from the series comprising fluorine, chlorine, bromine, methoxy or ethoxy.

In formula (I),
- $R^1$ especially preferably represents hydrogen, $C_1-C_4$-alkyl alkyl (which is optionally substituted by fluorine and/or chlorine or by methoxy or ethoxy); vinyl, 1-propenyl, allyl, or 1-butenyl (each of which is optionally substituted by fluorine and/or chlorine or by methoxy or ethoxy), or phenyl which is optionally monosubstituted to trisubstituted by identical or different substituents from the series comprising fluorine, chlorine, bromine, methoxy and ethoxy,
- A especially preferably represents dimethylene ($—CH_2CH_2—$) or trimethylene ($—CH_2CH_2CH_2—$),
- $R^2$ especially preferably represents methyl, ethyl, propyl or isopropyl,
- $R^3$ especially preferably represents ethyl, propyl, isopropyl, butyl, isobutyl, sec-butyl, pentyl, hexyl, heptyl or octyl, and
- $R^4$ especially preferably represents hydrogen, $C_1-C_4$-alkyl (which is optionally substituted by fluorine and/or chlorine or by methoxy or ethoxy); vinyl, 1-propenyl, allyl or 1-butenyl (each of which is optionally substituted by fluorine and/or chlorine or by methoxy or ethoxy), or phenyl which is optionally monosubstituted to trisubstituted by identical or different substituents from the series comprising fluorine, chlorine, bromine, methoxy and ethoxy.

The new compounds of the formula (I) are obtained when aza compounds of the general formula (II)

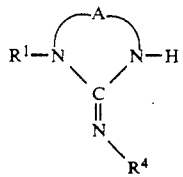

in which

A, $R^1$ and $R^4$ have the abovementioned meaning, or their hydrochlorides or hydrobromides are reacted with thiophosphoric acid O,S-diester chlorides of the general formula (III)

in which $R^2$ and $R^3$ have the abovementioned meaning, if appropriate in the presence of an acid acceptor and if appropriate in the presence of a diluent.

If, for example, 1-methyl-2-imino-imidazolidine and thiophosphoric acid O-ethyl ester S-sec-butyl ester chloride are used as starting substances, the course of the reaction in the process according to the invention can be described by the following equation:

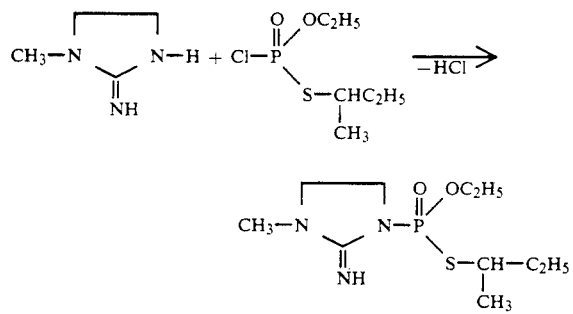

Formula (II) provides a general definition of the aza compounds to be used as starting substances in the process according to the invention for the preparation of compounds of the formula (I).

In formula (II), A, R and R preferably, or in particular, have those meanings which have already been mentioned above in connection with the description of the compounds of the formula (I) according to the invention as being preferred, or particularly preferred, for A, $R^1$ and $R^4$.

The starting substances of the formula (II) are known and/or can be prepared by processes known per se (compare, inter alia, DE-OS (German Published Specification) 2,140,405; DE-OS (German Published Specification) 2,144,013; U.S. Pat. No. 3,812,144; Synthesis 1987 (5), 460–466; J. Org. Chem., 44 (25), 4536–4543, 1979; Arzneim.-Forsch., 28 (10), 1676–1681, 1978).

Formula (III) provides a general definition of the thiophosphoric acid O,S-diester chlorides furthermore to be used as starting substances in the process according to the invention.

In formula (III), $R^2$ and $R^3$ preferably, or in particular, have those meanings which have already been mentioned above in connection with the description of the compounds of the formula (I) according to the invention as being preferred, or particularly preferred, for $R^2$ and $R^3$.

The starting substances of the formula (III) are known and/or can be prepared by processes known per se (cf. DE-A 2,527,308; DE-A 2,615,342; DE-A 2,642,982; DE-A 2,804,796).

The process according to the invention for the preparation of the compounds of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the process according to the invention are all acid binders which can customarily be used for reactions of this type. The following are preferably suitable: alkali metal hydrides and alkaline earth metal hydrides such as lithium hydride, sodium hydride, potassium hydride and calcium hydride, hydroxides such as sodium hydroxide and potassium hydroxide, alkali metal carbonates, alkali metal hydrogen carbonates, alkaline earth metal carbonates and alkaline earth metal hydrogen carbonates such as sodium carbonate, sodium hydrogen carbonate, potassium carbonate and potassium hydrogen carbonate as well as calcium carbonate, alkali metal acetates such as sodium acetate and potassium acetate, alkali metal alcoholates such as sodium tert-butylate and potassium tert-butylate, furthermore basic nitrogen compounds such as trimethylamine, triethylamine, tipropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out the process according to the invention, the reaction temperatures can be varied within a substantial range. In general, the process is carried out at temperatures between −20° C. and +80° C., preferably at temperatures between 0° C. and 50° C.

The process according to the invention is generally carried out under atmospheric pressure. However, it is also possible to carry out the process under increased or reduced pressure.

For carrying out the process according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the temperature required in each case. Working-up is carried out in each case by customary methods (compare the Preparation Examples).

The compounds of the formula (I) are suitable for combating animal pests, preferably arthropods and nematodes, in particular insects and nematodes in the soil encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus* corporis, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Antho. nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata,* Dacus oleae and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., Trichodorus spp.

The compounds of the formula (I) according to the invention are distinguished by an outstanding insecticidal and nematicidal activity. In particular when used against foliar insects which are harmful to plants and also against nematodes, they show a very potent action. The excellent (root-systemic) action against foliar insects and nematodes must be particularly emphasised.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

PREPARATION EXAMPLE

Example 1

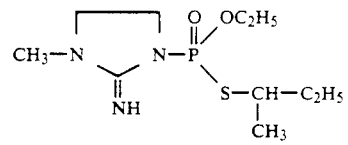

36 g (0.2 mol) of 1-methyl-2-imino-imidazolidine hydrobromide are introduced into 800 ml of dichloromethane and 320 g (0.8 mol) of 10 % strength NaOH, and 43.3 g (0.2 mol) of O-ethyl S-sec-butyl chlorothiophosphate are added dropwise at room temperature with vigorous stirring. After the mixture has been stirred for 30 minutes, the organic phase is separated off, dried over magnesium sulphate and concentrated under reduced pressure. The product is purified on silica gel (eluent ethyl acetate/ethanol 9:2). 13.8 g (24.7 % of theory) of O-ethyl S-sec-butyl 3-methyl-2-imino-1-imidazolidinylthiophosphate are obtained.

$^{31}$P NMR*): δ = 33.66; 33.61.

The compounds of the formula (I) which are listed below in Table 1 can be obtained analogously to the process described in Example 1 and taking into account the information in the process according to the invention $$R^1-N\underset{\underset{R^4}{\overset{\|}{C}}}{\overset{A}{\frown}}N-P\overset{O}{\underset{SR^3}{\diagdown}}OR^2 \quad (I)$$

TABLE 1

| Ex. No. | R¹ | —A— | R² | R³ | R⁴ | Physical Constant |
|---|---|---|---|---|---|---|
| 2 | CH₃ | —CH₂—CH₂— | —C₂H₅ | —C₄H₉ₛ | 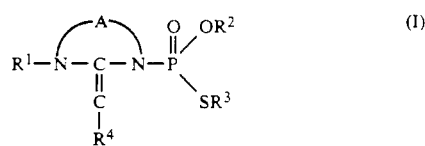 | $^{31}$P-NMR*): δ = 26. 80; 26. 86 |

TABLE 1-continued

| Ex. No. | $R^1$ | —A— | $R^2$ | $R^3$ | $R^4$ | Physical Constant |
|---|---|---|---|---|---|---|
| 3 | $CH_3$ | $-CH_2-CH_2-CH_2-$ | $-C_2H_5$ | $-C_4H_{9s}$ | 4-Cl-phenyl | $^{31}$P-NMR*): $\delta = 29.14; 29.36$ |
| 4 | H | $-CH_2-CH_2-$ | $-C_2H_5$ | $-C_4H_{9s}$ | phenyl | $^{31}$P-NMR*): $\delta = 28.41$ |
| 5 | $C_4H_{9n}$ | $-CH_2-CH_2-$ | $-C_2H_5$ | $-C_4H_{9s}$ | H | $^{31}$P-NMR*): $\delta = 27.59$ |
| 6 | phenyl | $-CH_2-CH_2-$ | $-C_2H_5$ | $-C_4H_{9s}$ | H | $^{31}$P-NMR*): $\delta = 27.63$ |
| 7 | $CH_3$ | $-CH_2-CH_2-$ | $-C_2H_5$ | $-C_6H_{13n}$ | H | |
| 8 | $CH_3$ | $-CH_2-CH_2-$ | $-C_2H_5$ | $-CH_2-C_4H_{9iso}$ | H | |
| 9 | $CH_3$ | $-CH_2-CH_2-$ | $-C_2H_5$ | $-CH_2-CH(C_2H_5)-C_2H_5$ | H | |
| 10 | $CH_3$ | $-CH_2-CH_2-$ | $-C_2H_5$ | $-CH_2-CH(C_2H_5)-C_4H_{9n}$ | H | |
| 11 | 3,4-dichlorophenyl | $-CH_2-CH_2-$ | $-C_2H_5$ | $-C_4H_{9s}$ | H | |
| 12 | phenyl-$CH_2-CH_2-$ | $-CH_2-CH_2-$ | $-C_2H_5$ | $-C_4H_{9s}$ | H | |
| 13 | H | $-CH(CH_3)-CH_2-$ | $-C_2H_5$ | $-C_4H_{9s}$ | H | |
| 14 | $CH_3$ | $-CH_2-CH_2-$ | $-C_2H_5$ | $-C_3H_7$ | H | |
| 15 | $CH_3$ | $-CH_2-CH_2-CH_2$ | $-C_2H_5$ | $-C_3H_7$ | H | |
| 16 | 2-Cl-pyridin-5-yl-$CH_2-$ | $-CH_2-CH_2-$ | $-C_2H_5$ | $-C_3H_7$ | H | |
| 17 | $CH_3$ | $-CH_2-CH_2-$ | $-C_2H_5$ | $-C_8H_{17n}$ | H | |
| 18 | $CH_3$ | $-CH_2-CH_2-$ | $-C_2H_5$ | $-C_7H_{15n}$ | H | |

*)The $^{31}$P NMR spectra were recorded in deuterochloroform ($CDCl_3$) with $H_3PO_4$ as the external standard.
The figure given is the chemical shift as $\delta$ value in ppm.

USE EXAMPLES

In the Use Examples, compound (A) listed below is used as comparison compounds:

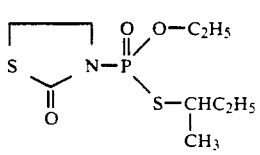

(A)

O-Ethyl S-(1-methylpropyl) (2-oxo-3-thiazolidinyl)-phosphorothioate/fosthiazate (disclosed in U.S. Pat. No. 4,509,182).

EXAMPLE A

Critical Concentration Test/Root-Systemic Action

Test insect: Phaedon cochleariae larvae
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (Brassica oleracea). The active compound can in this way be taken up from the soil by the roots of the plants and be transported into the leaves.

To demonstrate the root-systemic effect, the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, for example the compound according to Example 1 showed a highly superior activity compared with the prior art.

EXAMPLE B

Critical Concentration Test/Root-Systemic Action

Test insect: Myzus persicae
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (Brassica oleracea). The active compound can in this way be taken up from the soil by the roots of the plants and be transported into the leaves.

To demonstrate the root-systemic effect, the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, for example the compound according to Example 1 showed a highly superior activity compared with the prior art.

EXAMPLE C

Test for Duration of Action/Nematodes

Test nematodes: Meloidogyne incognita
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with the soil. The concentration of the active compound in the preparation is of practically no importance, only the amount by weight of active compound per unit volume of soil, which is given in ppm (mg/l), being decisive. 6 l pots are filled with the soil and allowed to stand at 15° C.

The soil is mixed again, and soil samples of 375 ccm are taken every 2 weeks, 125 ccm of highly infested namatode soil (Meloiogyne) is admixed to the treated soil, salad seeds are sown in, and these pots are cultured at a greenhouse temperature of 25° C.

After four weeks, the roots are examined for infestation with nematodes (root galls), and the degree of action of the active compound is determined as a percentage. The degree of action is 100% if infestation is avoided altogether, and it is 0% when the level of infestation is just as high as in the control plants in untreated, but similarly infested, soil.

In this test, for example the compound according to Example 1 showed a highly superior activity compared with the prior art.

EXAMPLE D

Test for Duration of Action/Nematodes

Test nematodes: Globodera rostochiensis
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with the soil. The concentration of the active compound in the preparation is of practically no importance, only the amount by weight of active compound per unit volume of soil, which is given in ppm (mg/l), being decisive. 6 l pots are filled with the soil and allowed to stand at 15° C.

The soil is mixed again, and soil samples of 375 ccm are taken every 2 weeks, 125 ccm of highly infested namatode soil (Globodera) is admixed to the treated soil, potato cuttings are planted, and these pots are cultured at a greenhouse temperature of 20° C.

After six weeks, the roots are examined for infestation with nematodes (cysts), and the degree of action of the active compound is determined as a percentage. The degree of action is 100% if infestation is avoided altogether, and it is 0% when the level of infestation is just as high as in the roots of the control plants from untreated, but similarly infested, soil.

In this test, for example the compound according to Example 1 showed a highly superior activity compared with the prior art.

We claim:
1. Phosphorylated diazacycloalkanes of the formula (I)

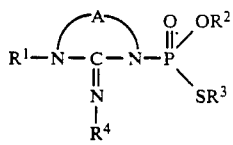

in which
- $R^1$ represents hydrogen; $C_1$-$C_8$-alkyl (which is optionally substituted by fluorine and/or chlorine or by $C_1$-$C_4$-alkoxy); $C_2$-$C_6$-alkenyl (which is optionally substituted by fluorine and/or chlorine or by $C_1$-$C_4$-alkoxy), or phenyl which is optionally monosubstituted to polysubstituted by identical or different substituents from the group consisting of halogen and $C_1$-$C_4$-alkoxy,
- A represents $C_2$-$C_4$-alkanediyl which is optionally monosubstituted or polysubstituted by identical or different substituents from the group consisting of methyl and ethyl,
- $R^2$ represents $C_1$-$C_8$-alkyl,
- $R^3$ represents $C_1$-$C_{12}$-alkyl and
- $R^4$ represents hydrogen; $C_1$-$C_8$-alkyl (which is optionally substituted by fluorine and/or chlorine or by $C_1$-$C_4$-alkoxy); $C_2$-$C_6$-alkenyl (which is optionally substituted by fluorine and/or chlorine or by $C_1$-$C_4$-alkoxy), or phenyl which is optionally monosubstituted to polysubstituted by identical or different substituents from the group consisting of halogen and $C_1$-$C_4$-alkoxy.

2. A pesticidal composition comprising a pesticidally effective amount of at least one phosphorylated diazacycloalkane of the formula (I) according to claim 1 and a carrier.

3. Phosphorylated diazacycloalkanes of the formula (I) according to claim 1, in which
- $R^1$ represents hydrogen; $C_1$-$C_6$-alkyl (which is optionally substituted by fluorine and/or chlorine or by methoxy or ethoxy); vinyl, propenyl or butenyl (each of which is optionally substituted by fluorine and/or chlorine or by methoxy or ethoxy), or phenyl which is optionally monosubstituted to trisubstituted by identical or different substituents from the group consisting of fluorine, chlorine, bromine, methoxy and ethoxy,
- A represents dimethylene or trimethylene, each of which is optionally monosubstituted or polysubstituted by identical or different substituents from the group consisting of methyl or ethyl,
- $R^2$ represents $C_1$-$C_6$-alkyl,
- $R^3$ represents $C_1$-$C_{10}$-alkyl and
- $R^4$ represents hydrogen; $C_1$-$C_6$-alkyl (which is optionally substituted by fluorine and/or chlorine or by methoxy or ethoxy); vinyl, propenyl or butenyl (each of which is optionally substituted by fluorine and/or chlorine or by methoxy or ethoxy), or phenyl which is optionally monosubstituted to trisubstituted by identical or different substituents from the group consisting of fluorine, chlorine, bromine, methoxy and ethoxy.

4. Phosphorylated diazacycloalkanes of the formula (I) according to claim 1, in which
- $R^1$ represents hydrogen; $C_1$-$C_4$-alkyl (which is optionally substituted by fluorine and/or chlorine or by methoxy or ethoxy); vinyl, 1-propenyl, allyl or 1-butenyl (each of which is optionally substituted by fluorine and/or chlorine or by methoxy or ethoxy), or phenyl which is optionally monosubstituted to trisubstituted by identical or different substituents from the group consisting of fluorine, chlorine, bromine, methoxy and ethoxy,
- A represents dimethylene ($-CH_2CH_2-$) or trimethylene ($-CH_2CH_2CH_2-$),
- $R^2$ represents methyl, ethyl, propyl or isopropyl,
- $R^3$ represents ethyl, propyl, isopropyl, butyl, isobutyl, sec-butyl, pentyl, hexyl, heptyl or octyl, and
- $R^4$ represents hydrogen; $C_1$-$C_4$-alkyl (which is optionally substituted by fluorine and/or chlorine or by methoxy or ethoxy); vinyl, 1-propenyl, allyl or 1-butenyl (each of which is optionally substituted by fluorine and/or chlorine or by methoxy or ethoxy), or phenyl which is optionally monosubstituted to trisubstituted by identical or different substituents from the group consisting of fluorine, chlorine, bromine, methoxy and ethoxy.

5. A method of combating pests comprising applying to the pests or their habitat a pesticidally effective amount of at least one phosphorylated diazacycloalkane of the formula (I) according to claim 1 and a carrier.

6. The method according to claim 5, wherein the pests combatted are insects or nematodes.

7. A phosphorylated diazacycloalkane having the formula:

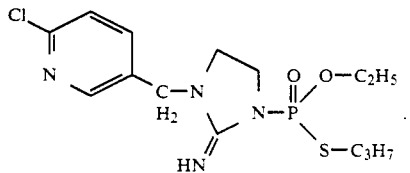

8. A pesticidal composition comprising a pesticidally effective amount of a phosphorylated diazacycloalkane according to claim 7 and a carrier.

9. A method of combating pests comprising applying to the pests or their habitat a pesticidally effective amount of a phosphorylated diazacycloalkane according to claim 7 and a carrier.

10. The method according to claim 9, wherein the pests combatted are insects or nematodes.

* * * * *